US00PP23359P3

(12) United States Plant Patent
Gmitter, Jr.

(10) Patent No.: US PP23,359 P3
(45) Date of Patent: Jan. 29, 2013

(54) MANDARIN TREE NAMED '950'

(50) Latin Name: *Citrus reticulata*
Varietal Denomination: 950

(75) Inventor: Frederick G. Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 13/136,684

(22) Filed: Aug. 8, 2011

(65) Prior Publication Data

US 2011/0302679 P1 Dec. 8, 2011

(51) Int. Cl.
*A01H 5/00* (2006.01)

(52) U.S. Cl. ..... Plt./202

(58) Field of Classification Search ..... Plt./201, Plt./202

See application file for complete search history.

*Primary Examiner* — Howard Locker

(74) *Attorney, Agent, or Firm* — Jondle & Associates, P.C.

(57) ABSTRACT

A new mandarin hybrid tree particularly distinguished by having dense foliation; bearing fruit that are attractive in appearance with excellent eating quality; has lateral branching with lower angle plant habit; a round tree shape; and nearly seedless fruit is disclosed.

5 Drawing Sheets

Genus and species: *Citrus reticulata.*
Variety denomination: '950'.

BACKGROUND OF THE NEW PLANT

The invention relates to a new and distinct variety of mandarin *Citrus reticulata* hybrid tree named '950'. '950' is a very vigorous tree that produces nearly seedless fruit and has a non-pungent peel oil. '950' usually ripens from the end of November to late January in central Florida.

'950' originated as a single plant from a cross conducted in March of 1991 in Lake Alfred, Fla., between 'LB8-8' (unpatented) and 'Fortune' (unpatented). Parent 'LB8-8' is a hybrid of a 'Clementine' and 'Minneola tangelo', and parent 'Fortune' has been reported to be a hybrid of 'Algerian Clementine' and unknown. Asexual propagation by budding in Lake Alfred, Fla. has shown that all distinguishing features and characteristics of the fruit and tree remain true to the original seedling tree and are in firmly fixed form.

Plant Breeder's Rights for this cultivar have not been applied for. '950' has not been made publicly available more than one year prior to the filing of this application.

SUMMARY OF THE INVENTION

The new and distinct variety of mandarin hybrid (tangerine) tree bears fruit that ripens from the end of November to late January in central Florida. The trees usually bloom around March to early April in central Florida, depending on the season, and they grow in a moderately vigorous manner. The fruit of '950' trees are nearly seedless, tend to be a bit smaller in diameter (between 55 mm to 65 mm) than fruit of 'LB8-8', have a round shape, moderate acidity, an orange color internally and an orange-red color externally, and have excellent eating quality. The fruit are juicy, but can be easily peeled.

The following are the most outstanding and distinguishing characteristics of this new cultivar when grown under normal horticultural practices in Florida.

1. Dense foliation;
2. Bearing fruit that are attractive in appearance with excellent eating quality;
3. Lateral branching with lower angle plant habit;
4. Round tree shape; and
5. Nearly seedless fruit.

DESCRIPTION OF THE PHOTOGRAPHS

This new mandarin tree is illustrated by the accompanying photographs which show the tree's form, foliage and fruit. The photographs are of a tree growing on its own roots. The colors shown are as true as can be reasonably obtained by conventional photographic procedures. The photographs are of a tree approximately 10-years old.

FIGS. 1-5 were taken in Spring and Fall 2008.

DESCRIPTION OF THE NEW CULTIVAR

Figure 1:
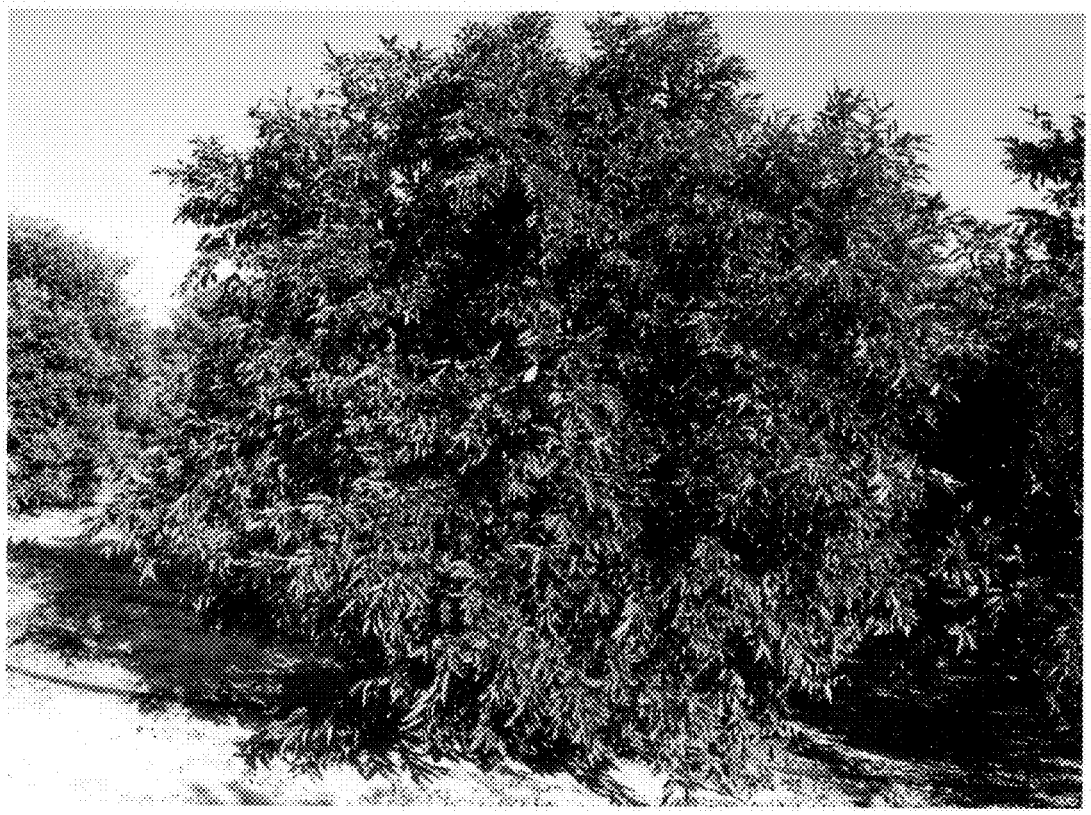
FIG. 1 shows the overall plant habit including foliage and fruit taken in the spring-time.
Figure 2:
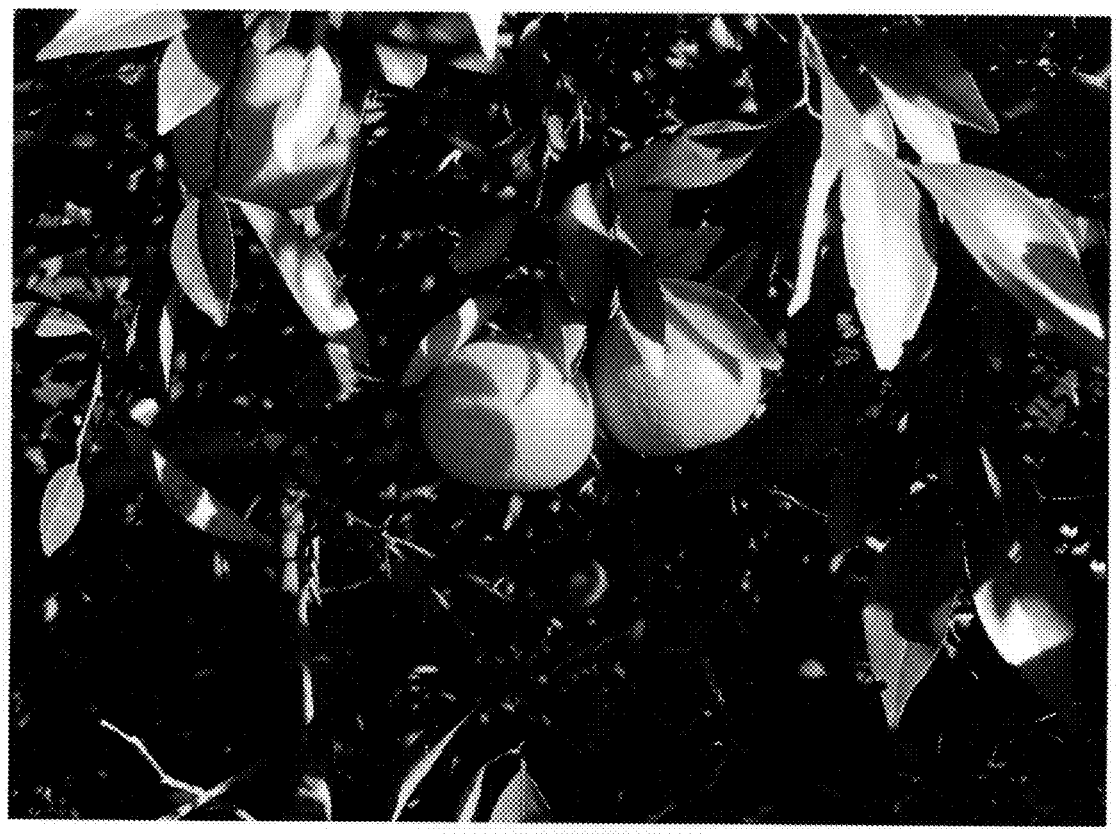
FIG. 2 shows mature fruit hanging on the tree.
Figure 3:
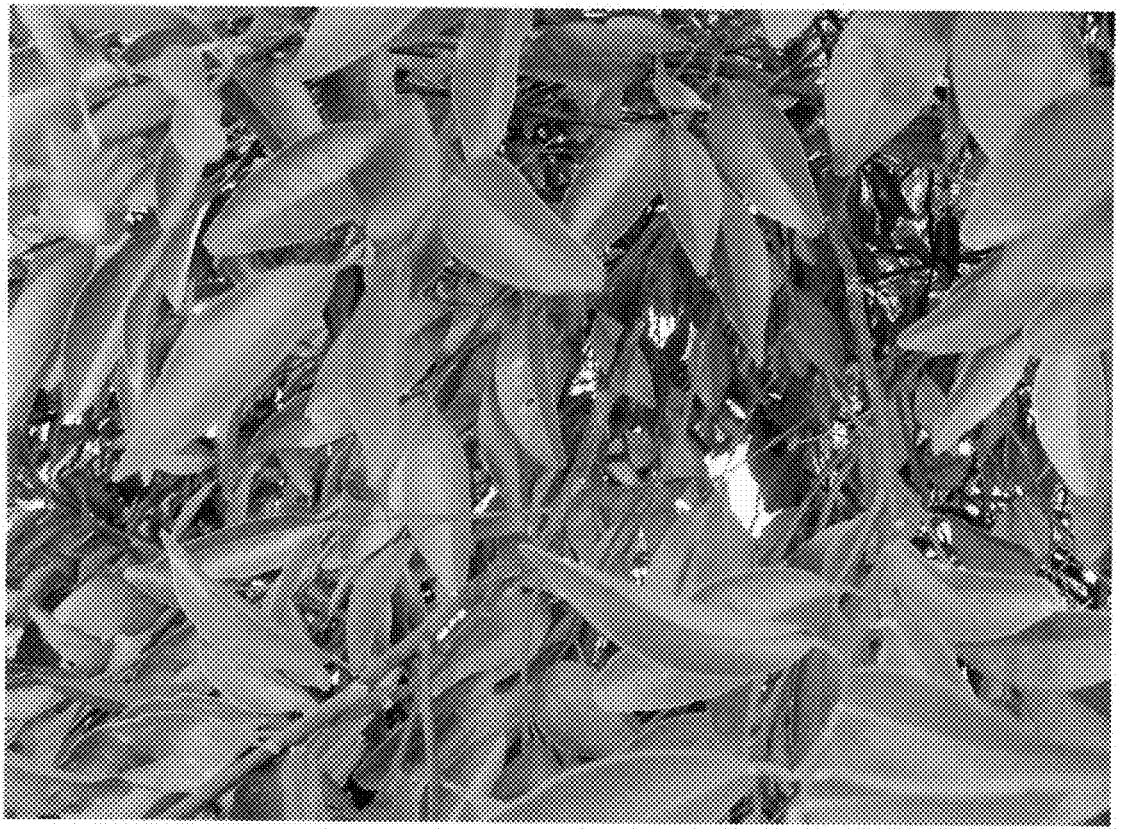
FIG. 3 shows a close-up of the mature leaves.
Figure 4:
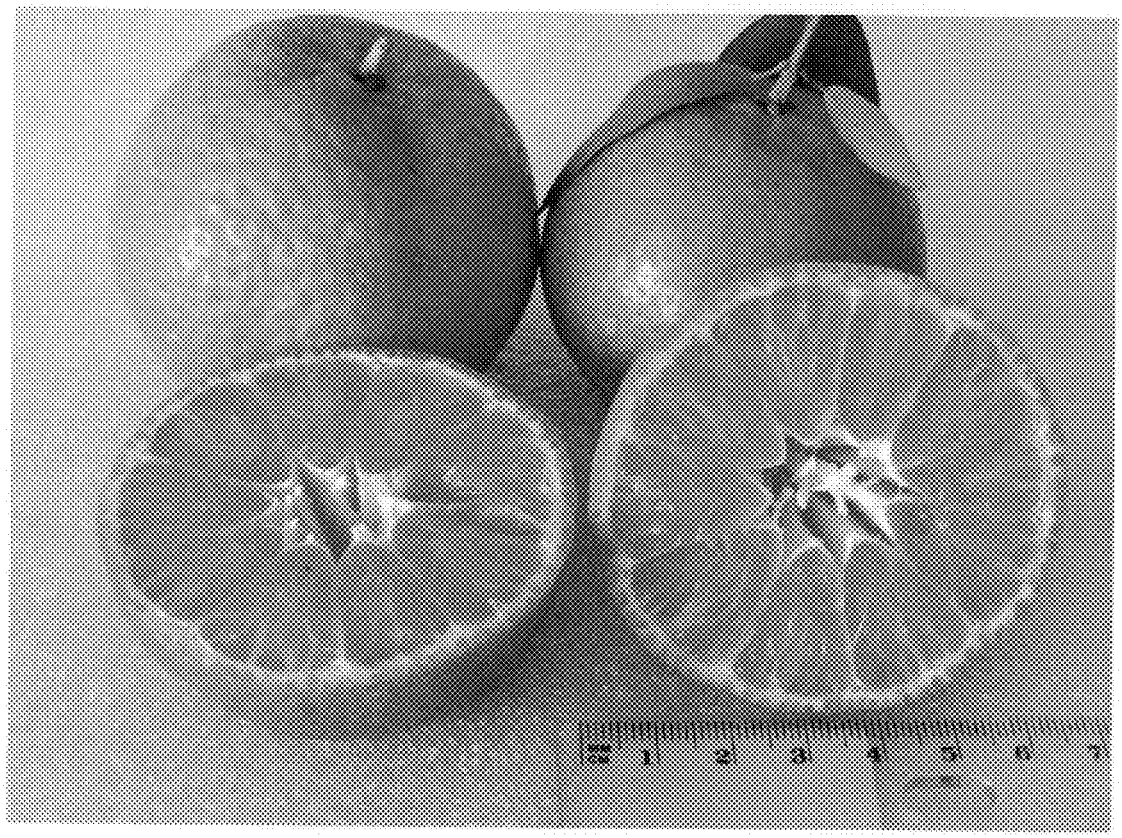
FIG. 4 shows a close-up of the mature fruit with the rind present and cross-sectional view of the fruit when cut in the center.
Figure 5:
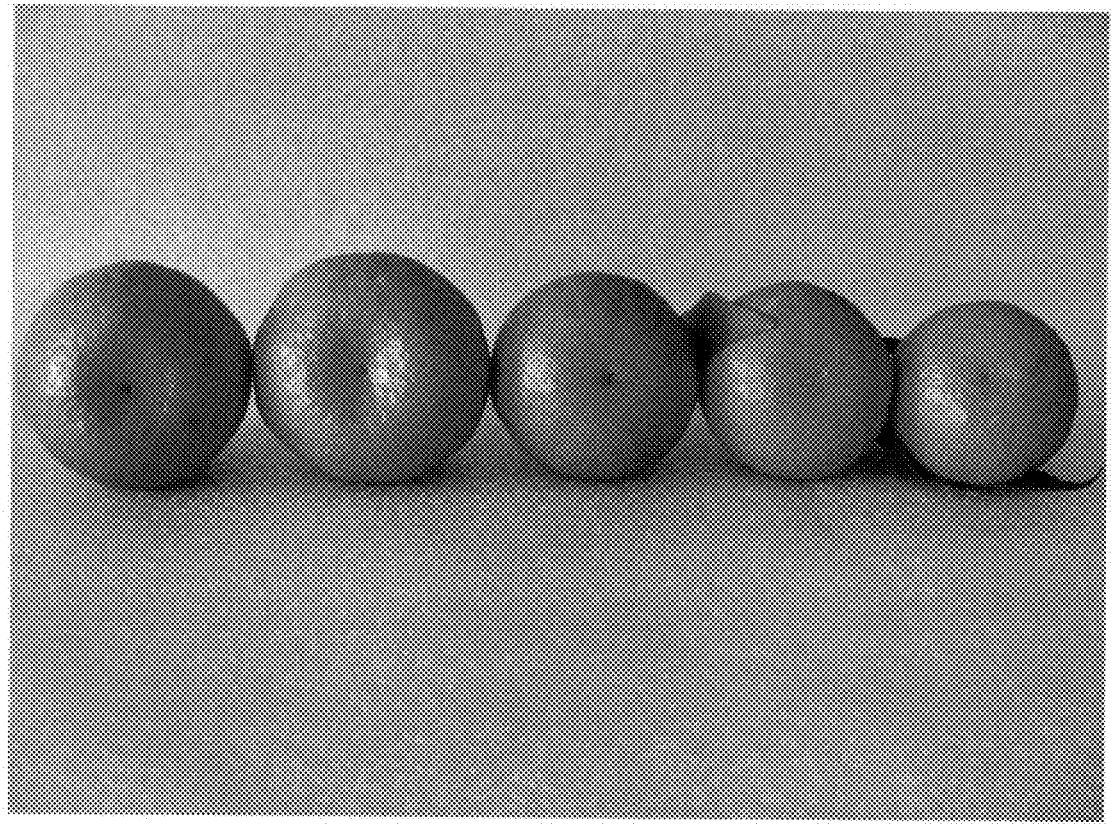
FIG. 5 shows an additional close-up of the mature fruit with the rind present.

The following detailed description sets forth the distinctive characteristics of '950'. The present botanical description was taken from an individual 10-year-old tree grown on its own roots at the Riley research block near Haines City, Fla. The colors (except those in common terms) are described from R.H.S. Colour Chart published by The Royal Horticultural Society in London (second edition), in association with the Flower Council of Holland.

DETAILED BOTANICAL DESCRIPTION

Classification:
*Botanical.—Citrus reticulata.*
*Common name.*—Mandarin hybrid or Tangerine.

Parentage:

*Female parent.*—'LB8-8' (unpatented).

*Male parent.*—'Fortune' (unpatented).

Tree:

*Ploidy.*—Diploid.

*Size.*—Medium with a height of 3.0 m at 10 years old.

*Tree spread.*—4.3 m if un-pruned.

*Vigor.*—Vigorous, growing shoots of 30.0 cm or more typically from spring flush on current tree.

*Density.*—Canopies are quite dense.

*Form.*—The shape of the tree is round with lateral branches toward low medium angles without fruiting. Branches with fruits exhibit drooping.

*Growth habit (current season).*—Lateral branching with lower angle plant habit.

Trunk and branches:

*Trunk diameter.*—12.2 cm measured at 30.0 cm above the ground.

*Trunk texture.*—Smooth.

*Trunk bark color.*—RHS 197A (greyed-green); irregularly striated with RHS 189B (greyed-green).

*Crotch angle.*—First tree crotch formed 60 degrees angle, and second crotch formed 20 and 40 degree angles.

*Branch length.*—3.6 m from the first crotch to the tip of the leaf branch.

*Branch texture.*—Relatively smooth and without thorns or spines.

*Branch color.*—RHS N137B (green).

*Branch diameter (measured on stems of hardened wood from previous growth flush).*—4.0 mm to 5.0 mm.

Leaves:

*Size (lamina average).*—Length: 71.5 mm. Width: 32.5 mm. L/W ratio: 2.2.

*Thickness.*—Regular and average for commercial mandarin hybrids.

*Type.*—Simple.

*Shape.*—Elliptical.

*Apex.*—Retuse.

*Base.*—Acute.

*Margin.*—Entire, smooth and slightly undulate.

*Surface.*—Upper surface: Glabrous. Lower surface: Medium veins that are pinnately netted.

*Color.*—Upper surface (adaxial): Range from RHS 143B (green) to RHS N137A (green). Lower surface (abaxial): Range from RHS 145A (yellow-green) to RHS 143B (green).

*Petiole.*—Shape: Brevipetiolate (shorter than leaf lamina); junction between petiole and lamina is articulate. Shape (petiole wing): Obovate. Length: 12.0 mm to 13.0 mm. Width: 2.0 mm to 2.3 mm. Color: RHS 143A (green).

Flowers:

*Type.*—Hermaphrodite, non self-fertile.

*Bearing.*—Flower grown from leaf axillaries in cluster or single. Each cluster consisted of 3 to 4 flowers. One flower branch consists of 3 to 4 flower clusters.

*Diameter (fully opened).*—28.2 mm to 29.0 mm.

*Depth.*—11.5 mm to 12.4 mm.

*Flower bud.*—Length: Immature: 1.8 mm to 2.0 mm. Mature: 11.1 mm. Diameter: Immature: 2.0 mm. Mature: 5.3 mm. Shape: Immature: Round and dome. Mature: Elongated olive. Color: Immature: RHS 144D (yellow-green). Mature: RHS NN155C (white) with RHS N144D (yellow-green) spots distributed on the surface of the petal.

*Petals.*—Shape: Flat spatula. Apex: Smooth acute. Base: Even obtuse. Number: 5. Color: Upper surface: RHS 155C (white) to RHS 155B (white). Lower surface: RHS NN155C (white) and RHS N144D (yellow-green). Length: 13.5 mm. Width: 4.1 mm. Margin: Smooth.

*Sepal.*—Number: 5. Shape: Delta shaped with acute angle at apex. Length: 2.0 mm to 2.1 mm. Width: 2.1 mm. Apex shape: Acute angle at apex. Margin: Smooth. Color: Upper surface: RHS 142D (yellow-green). Lower surface: RHS 150D (yellow-green).

*Pedicel.*—Length: 4.8 mm. Diameter: 0.7 mm to 0.8 mm. Color: RHS 143B (green) to RHS 143A (green).

*Blossom period.*—First bloom: Early March in Central Florida. Full bloom: Mid March to early April. Fragrance: Moderate intensity, typical of most mandarin cultivars.

Reproductive organs:

*Stamen.*—Length: 8.2 mm. Number: 17. Color: RHS 16B (yellow-orange).

*Anther.*—Width: 0.7 mm. Length: 2.0 mm to 2.1 mm. Anther filament length: 6.1 mm average.

*Pistil.*—Number: 1. Length: 6.1 mm. Color: RHS 142D (green). Style length: 3.8 mm to 4.1 mm average. Style diameter: 0.75 mm. Style color: RHS 142D (green). Ovary shape: Oval. Ovary diameter: 1.8 mm. Ovary color: RHS 143C (green).

*Pollen amount.*—Low.

*Pollen color.*—RHS 13A (yellow).

Fruit:

*Size.*—Uniform.

*Weight (per individual fruit).*—82.0 g to 120.0 g.

*Length.*—57.2 mm to 65.0 mm.

*Width.*—52.8 mm to 60.0 mm.

*Shape.*—Round.

*Shape (cross-section).*—Round.

*Apex.*—Truncated.

*Apex cavity diameter.*—1.0 mm.

*Base.*—Flat with very short neck and wrinkled.

*Base cavity diameter.*—4.8 mm.

*Diameter of the connecting stem.*—2.5 mm.

*Color of the connecting stem.*—RHS 198D (greyed-green).

*Harvesting data.*—End of November to late January.

*Lastingness of fruit on the tree.*—3 to 5 weeks.

Rind:

*Adherence.*—Albedo (mesocarp) to flesh (endocarp) is medium low, compared to other commercial hybrid varieties, easy to peel. Low adherence is evenly distributed through the whole fruit.

*Thickness.*—2.0 mm, relatively thin compared to other commercial mandarin hybrid varieties.

*Texture.*—Smooth.

*Color.*—Flavedo (epicarp): RHS 25A (orange). Albedo (mesocarp): Range from between RHS 24C (orange) to RHS 24B (orange-red).

*Stylar end.*—Closed.

Flesh:

*Number of segments.*—Average between 9 and 12 per fruit.

*Segment walls.*—Medium firm with sufficient strength to maintain integrity as separated.

*Juice*.—Abundant.

*Color*.—Uniformly RHS 25A (orange).

*Texture*.—Firm to medium soft.

*Vesicles*.—Medium thick compared with other mandarin varieties. Length: 8.0 mm to 10.0 mm. Width: 2.0 mm to 3.0 mm.

*Eating quality*.—Soluble solids (average): 13.1 Brix. Acidity (average): 0.82%. Ratio: 15.98.

Seeds:

*Type*.—In many cases, seeds appear to be monoembryonic. In fewer cases, some fruit also produce polyembryonic seeds.

*Number*.—Ranges from 0 to 2, most fruit being seedless.

*Shape*.—Most normal and fully developed seeds are ventricose/swollen shaped. Undeveloped seeds are mostly clavate club-shaped.

*Seed length*.—9.0 mm.

*Seed width*.—5.5 mm.

*Seed coat color*.—Outer surface: RHS 13C (yellow) and smooth. Inner surface: RHS 165D (greyed-orange).

*Cotyledon color*.—RHS 138C (green).

Disease and pest resistance: None observed.

COMPARISON WITH PARENTAL AND KNOWN CULTIVARS

'950' differs from the female parent 'LB8-8' (unpatented) by being smaller in diameter, 55.0 mm to 65.0 mm, compared to 70.0 mm to 130.0 mm. Additionally, '950' has a round shape, whereas 'LB8-8' has a pyriform shape, and '950' has nearly seedless fruit, whereas 'LB8-8' has seedy fruit. In addition, 'LB8-8' produces fruit with extremely low acidity, compared to '950'.

'950' differs from the male parent 'Fortune' (unpatented) by having moderate acidity, whereas 'Fortune' has high acidity. Additionally, '950' has mid-season maturity, whereas 'Fortune' has late season maturity, and '950' has nearly seedless fruit, whereas 'Fortune' has seedy fruit.

Compared to the commercial variety 'Clementine' (unpatented), '950' has mid-season maturity, whereas 'Clementine' has early season maturity, and '950' has non-pungent peel oil, whereas 'Clementine' has pungent peel oil. Additionally, '950' is nearly seedless even with abundant cross pollination, whereas 'Clementine' is seedy upon cross pollination.

I claim:

1. A new and distinct cultivar of mandarin hybrid tree as shown and described herein.

* * * * *